United States Patent [19]

Lehmann et al.

[11] Patent Number: 4,863,603

[45] Date of Patent: Sep. 5, 1989

[54] FILTER UNIT FOR SEPARATING PRECIPITATES CONTAINING CHOLESTEROL

[75] Inventors: Hans-Dieter Lehmann, Zimmern-Bisingen; Heinz-Gerhard Köhn, Dransfeld, both of Fed. Rep. of Germany

[73] Assignee: Sartorius GmbH, Fed. Rep. of Germany

[21] Appl. No.: 176,669

[22] Filed: Apr. 1, 1988

[30] Foreign Application Priority Data

Apr. 9, 1987 [DE] Fed. Rep. of Germany ....... 3712044

[51] Int. Cl.⁴ .................... A61M 5/00; E01D 29/00
[52] U.S. Cl. .................................. 210/489; 210/492; 210/493.1; 210/927
[58] Field of Search ................ 604/123, 122, 126, 67, 604/151-153; 128/DIG. 12, DIG. 13; 210/493.2, 493.1, 488, 489, 490, 491, 492, 493.3, 493.5, 496, 927

[56] References Cited

U.S. PATENT DOCUMENTS 4,579,698 4/1986 Meyering et al. ............... 210/493.2
4,642,098 2/1987 Lundquist .................... 120/DIG. 12

Primary Examiner—Frank Sever
Attorney, Agent, or Firm—Eric P. Schellin

[57] ABSTRACT

A multilayer filter medium (6) is used for separating precipitates containing cholesterol from blood plasma which consists of at least one open filter medium (7) which adsorbs precipitate and of a microporous membrane (9) which controls the pressure conditions in the filter element, whereby the layer (7) which specifically adsorbs the precipitate is hydrophobic and the microporous membrane (9) is hydrophilic. In addition, a positively charged adsorption medium (9) is provided on the side of the microporous membrane (8) facing away from the hydrophobic adsorption medium (7). In this manner, a large adsorption area is created and kept accessible for the precipitates and for heparin.

16 Claims, 3 Drawing Sheets

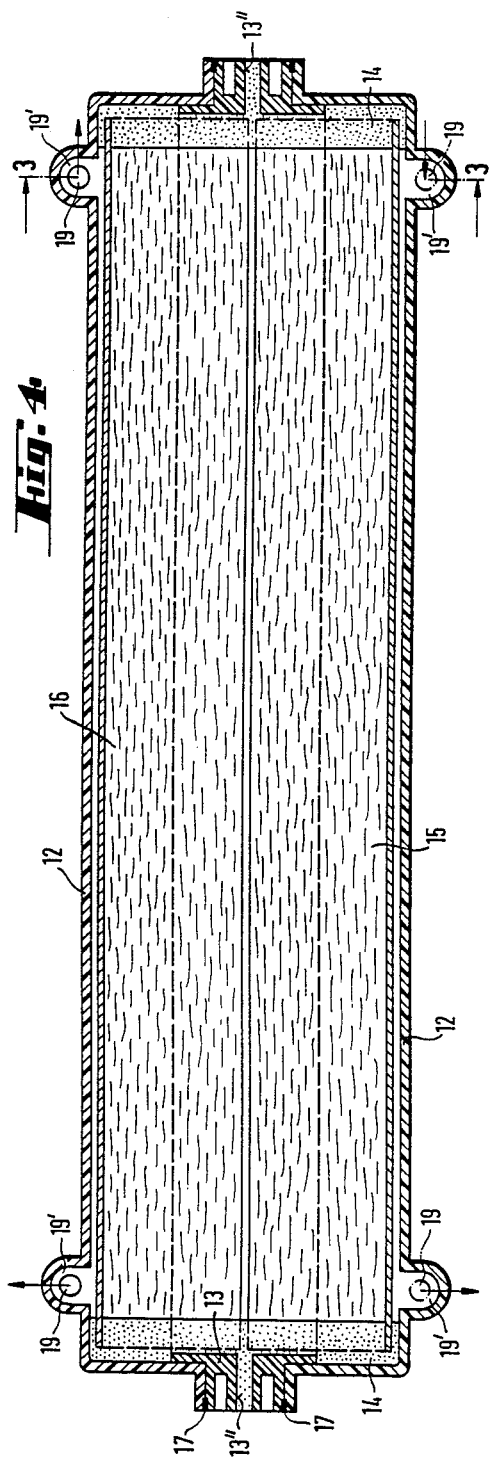
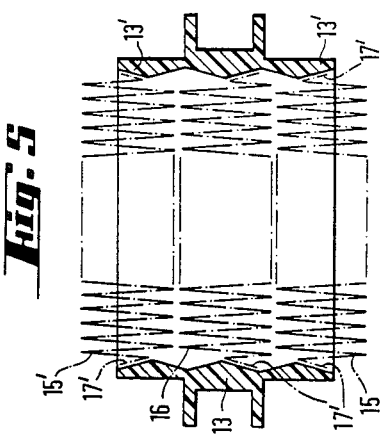
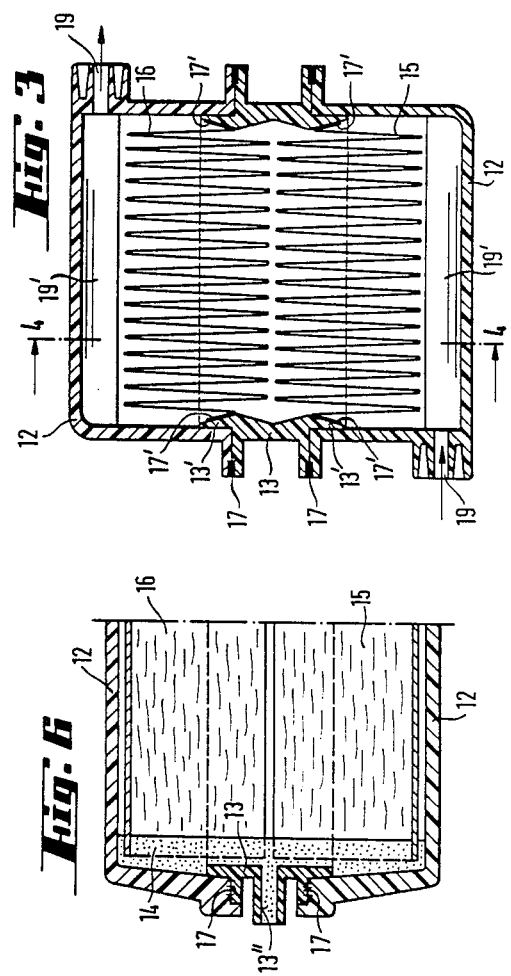

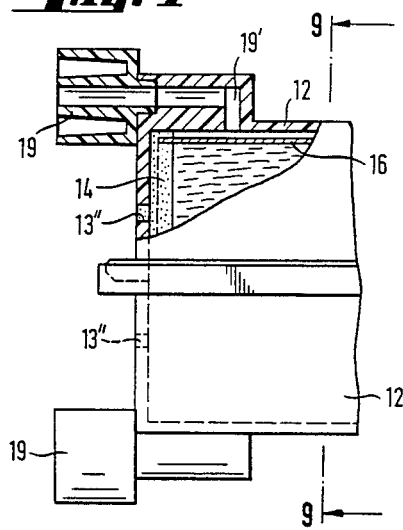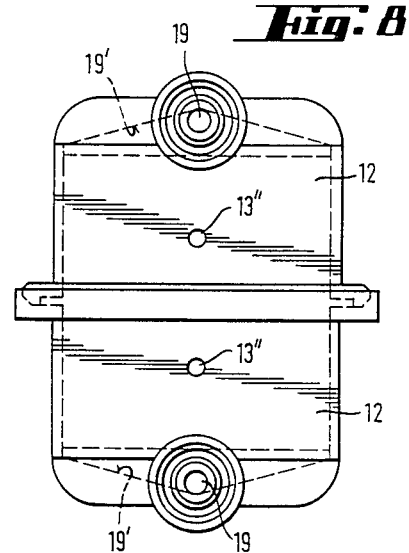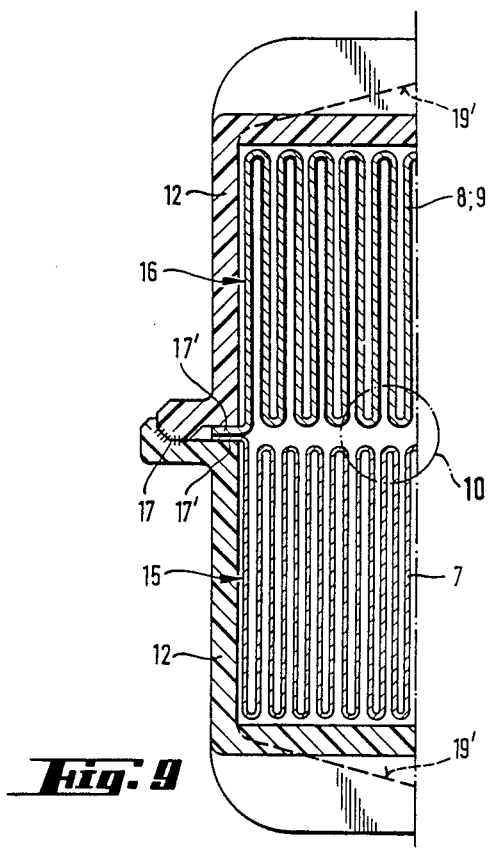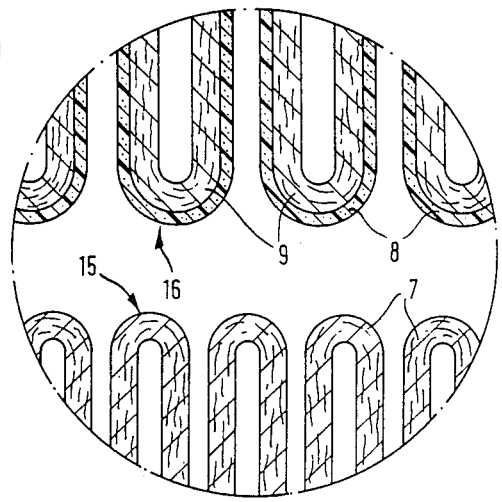

FILTER UNIT FOR SEPARATING PRECIPITATES CONTAINING CHOLESTEROL

The invention relates to a multi-layer filter element for separating precipitates containing cholesterol from blood plasma and its usage in dynamic filtration or in filtration according to the cross-flow principle.

BACKGROUND OF THE INVENTION

The content of low-density lipoproteins (LDL) in human blood plasma is positively and that of high-density lipoproteins (HDL) negatively correlated with the risk of cardiac infarcation. Malchesky et al. (U.S. Pat. No. 4,350,156 and EP-A 0041350) therefore suggest that patients suffering from hypercholesteremia be treated using plasmapheresis. They provide thereby that the blood components containing cholesterol be rendered separable by means of suitable measures, e.g. the addition of heparin, and be separated by filtration from the blood plasma.

Seidel et al. have used an elegant method for this according to DE-OS 31 35 814. Their method is capable of holding HDL in the plasma and of separating LDL together with the fibrinogen which is pathologically elevated to an excess degree in patients at risk of cardiac infarction. They make use of the fact in this connection that HDL and LDL differ both in their molecular weights and also in their HLB (hydrophilic-lipophilic balance) (A. K. J. Koumans, A. P. Wildschut, "Nutrition and Atherosclerosis: Some Neglected Aspects", Clin. Cardiol 8, 1985, p. 549).

|  | HDL | LDL |
|---|---|---|
| Molecular weight (Dalton) | approx. 400,000 | approx. 2-3.5 mio |
| portion of cholesterol (%) |  |  |
| i.e. hydrophobic = lipophilic | 25 | 47 |
| Protein (%) | 22 | 25 |
| hydrophilic | 75 | 53 |
| Lecithin (%) | 53 | 28 |

In this method, the blood plasma gained by plasmapheresis is diluted and lowered in pH. This gives the lipoproteins such as fibrinogen positive excess charges which complex with the heparin added in the buffer as polyanion. LDL precipitates as complex with a high hydrophobic portion whose lardaceous nature is unfavorable for filtering. For this reason, Rosskopf et al. suggest in DE-OS 33 10 727 for its separation a pressureless cross-flow filtration with the aid of a large-area filter cartridge in which a polycarbonate membrane is used. Almost two $m^2$ membranes are used for this filter in application because a large part of the area is blocked by the precipitate.

From a medical standpoint, the large dead volume associated with this filter design is a disadvantage. In spite of the plasma being diluted with acetate buffer, a large volume of plasma ia removed from the body which must be returned to the greatest extent possible at the end of the treatment.

An urgent requirement of the described method is the necessity of removing the excess heparin from the blood plasma again in which the precipitation was performed. It is held fast in the methods according to DE-OS 18 35 814, Seidel et al. in an adsorption column to an anion exchanger. Then, the purified plasma, corrected in pH and in volume, is returned to the patient together with the cellular blood components.

The invention is therefore based on the designing of an efficient filter for separating the heparin complexes of pathological plasma components. A high performance density, that is, small volume, is intended to minimize the extracorporeal plasma volume and nevertheless achieve the required capacities. A additional problem is to unite the separation of precipitate and the separation of the heparin excess in one process in the multi-stage method according to the state of the art, e.g. according to DE-OS 31 35 814.

SUMMARY OF THE INVENTION

The invention solves this problem in in that adsorption surfaces are connected in front of and optionally after a separating membrane. These large-area adsorption surfaces for the precipitates and/or for heparin are as readily accessible as possible. They assure, along with large adsorption capacity, a pressureless passage of the liquid to be filtered even if they have already been charged to a great extent with the materials to be adsorbed. The pressure conditions in this filter are determined by the microporous membranes placed between the adsorption surfaces. This prevents, according to the invention, the formation of canals through the open adsorbent, thus preventing precipitation breakthroughs.

According to the invention, the combination in the multi-layer adsorption filtration composite is designed so that hyrophobic fleece is contacted by the plasma with the precipitate. The next layer is a microporous membrane which is as hydrophilic as possible, followed by an adsorption layer with positive charges. This can be e.g. a membrane of DEAE [diethylaminoethanol-transl.] cellulose or a fleece with DEAE groups (e.g. DEAE paper of the Serva company) or other positively charged membranes such as e.g. those sold by the Pall company with the designation Posidyne or AMF-Cuno with the designation Zetaplus. A particularly preferred embodiment is constituted by a continuous-filament fleece with positive charges like that which can be produced from uncharged continuous-filament fleeces in analogy with the outfitting of membranes in the patents of the firms of Pall and AMF-Cuno.

Filters with the multi-layer filter media of the invention can be produced in a known manner in the form of pleated filters (e.g. as in a filter according to DE-OS 33 44 374 of the Sartorius company) or in other configurations which make a cross-flow application possible. Embodiments are preferred with a high performance density, e.g with small dead volume.

A filter which corresponds in its outer design to a folded filter element according to DE-OS 33 44 374 of the Sartorius GmbH company consists of a pleated membrane between two supporting fleeces. The device is divided into two chambers by means of sealing between the filtration layers and the housing with sealing compound (e.g. polyurethane). The plasma in which the precipitate was precipitated is recirculated through the first chamber.

The filter fleeces are hydrophobic continuous fleeces of polyester with an areal weight of approximately 50 $g/m^2$ and a filament thickness of approximately 2 detex. The microporous membrane constituting the following layer consists of a polyamide 6.6 membrane with pore sizes of 0.45 and 0.8 $\mu m$. At a membrane area of 0.2 $m^2$, the hydrophobic adsorption surface installed on the precipitate side was 3.5 $m^2$.

A precipitate was precipitated in outdated human plasma according to DE-OS 31 35 814 with acetate buffer and heparin. The plasma with the yellowish, milky precipitate was recirculated through the first chamber of the filter. The inlet-side pressure on the filter was 0.04 bar. In example 1, (pore width 0.45 μm), a hydrostatic pressure difference of approximately 50 cm water column was sufficient for filtration, in example 2 (pore width 0.8 μm), the system was emptied out at a height difference of 5–10 cm already. The purified plasma was clear and slightly yellowish.

The results are collated in table 1.

TABLE 1

| | Specimen Nr. | Cholesterol (mg/dl) | Triglycerides (m/dl) | Total protein (g/dl) | Albumin (g/dl) |
|---|---|---|---|---|---|
| Initial specimen | 0 | 150 | 70 | 6.0 | 3.8 |
| Filtrate from Filter with 0.8 m | 1 (start) | 34 | 18 | 5.0 | 2.8 |
| | 2 (15 min) | 32 | 16 | 4.8 | 2.6 |
| | 3 (end) | 32 | 16 | 4.6 | 2.6 |
| Filtrate from Filter with 0.45 m | 1B (start) | 48 | 26 | 6.0 | 3.6 |
| | 2B (15 min) | 46 | 26 | 6.0 | 3.6 |
| | (end) | 46 | 26 | 6.0 | 3.4 |

In a further experiment, heparin was eliminated during filtration:

The experiment was performed as in example 2. An open DEAE paper of the Serva company (Nr. 430652) was used behind the nylon membrane. The clear plasma was free of heparin.

The concept of the invention can be realized in various embodiments. The possibilities known according to the state of the art of locating filter elements in various arrangements in very different housings are therefore explained in the following schematic representation.

BRIEF DESCRIPTION OF THE DRAWINGS

FIG. 3 schematically shows a cross section through the filter element with housing along line 3—3 in FIG. 4.

FIG. 4 shows a longitudinal section through the unit along line 4—4 in FIG. 3.

FIG. 5 shows a cross section through a filter element consisting of three fold blocks and preassembled in an annular housing part.

FIG. 6 shows a modified embodiment of the housing design.

FIG. 7 shows a housing end with modified fluid connections in a side view in partial section of a preferred embodiment.

FIG. 8 shows a front view thereof.

FIG. 9 shows a detailed section through the housing connection on the longitudinal asides with inclusion of the end folds of the filter elements.

FIG. 10 is an enlargement of a portion of the cross-section of FIG. 9.

DETAILED DESCRIPTION OF THE INVENTION

Figure 1:
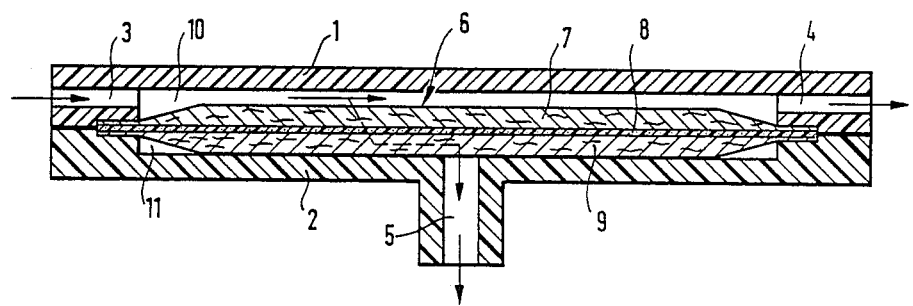
FIG. 1 shows a schematic section through a housing with installed filter element.

According to FIG. 1, filter element 6 is clamped in a sealing manner by its edges between the two filter housing parts 1,2.

Filter element 6 separates retentate area 10 of the filter housing with two connections 3,4 from permeate area 11 with permeate outlet 5.

Figure 2:
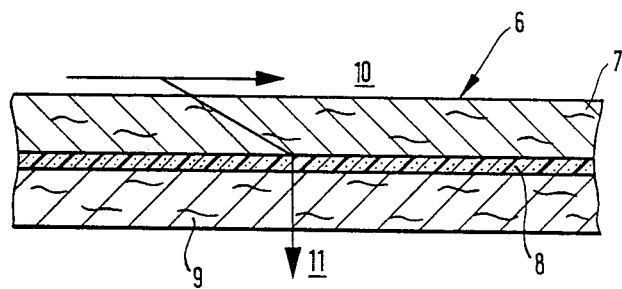
FIG. 2 shows a schematic cross section through the filter element of the invention.

According to FIG. 2, filter element 6 consists of hydrophobic fleece 7 with precipitate-absorbing properties, microporous and hydrophilic membrane 8 which follows downstream and controls the pressure conditions in the filter element and of hydrophilic support fleece 9 with draining action which is preferably positively charged. The blood plasma to be treated recirculates in retentate chamber 10 and flows over filter element 6 according to the cross-flow principle through fluid connections 3,4. The precipitate is removed via permeate outlet 5.

The practical embodiments described in the following show filter units with a large filter area and adsorption area in a close space, large packing density and very small dead volume.

According to FIGS. 3 and 4, the filter unit consists of the two identical housing shells 12 with connections 19 which change into liquid distributors 19' running in the transverse direction of the housing.

Annular housing part 13 is located between both housing shells 12, is provided with sealing flanges and is connected in a sealing manner to corresponding sealing flanges of housing shells 12, whereby seal 17 can be produced either by ultrasound welding or by adhesion. Hydrophobic filter element 15 which adsorbs the precipitate is located in pleated form in lower housing shell 12, runs with its fold edges in the longitudinal direction of housing 12,13 and its end folds 17' contact sealing lips 13' of annular housing part 13 in a sealing manner. In the same manner, pleated membrane filter element 16 is connected in downstream in the direction of flow which element allows the actual permeate to be extracted to pass through. The front areas of both filter packets 15,16 are sealed in housing 12,13 by means of sealing compound 14 which can be brought in through housing openings 13" e.g. in central housing part 13.

The medium to be filtered flows into flows housing shell 12 into the one connection 19, flows over the folds of adsorbing filter elements 15 running in a longitudinal direction and leaves the lower housing shell through the other outlet 19, whereby the overflow, i.e., flowing of the medium over 15, takes place according to the cross-flow principle. The constituents of the liquid not adsorbed by filter element 15 penetrate filter element 15 and penetrate for their part the actual membrane filter element 16 according to the static principle of filtration, whereby the permeate can be drawn off from the one or the other or from both connections 19 of the upper housing shell.

In the embodiment of FIG. 5, the actual membrane filter element 16 is followed by another filter element 15', likewise in pleated form with adsorbing properties. Three filter elements can be placed by reducing the pleating height of the individual folds without having to change the dimensions of the housing or the forms.

FIG. 6 shows a detail concerning the connection of annular housing part 13 to the two shell-shaped housing parts 12 and the arrangement of openings 13" for injecting flowable and hardenable sealing compound 14 for the front sides of fold packets 15, 15',16 and also for possibly bringing in sealing compound 14 for sealing the end folds in a longitudinal direction.

The arrangement of an annular housing part 13 between two identical shell-shaped housing parts 12 has the advantage that filter units with different filter areas can be created, if necessary, by annular housing parts with different heights by virtue of the fact that the pleating height of the folds is varied and the filter units can be constructed of identical housing shells 12 and annular housing parts 13 with different heights.

In the preferred embodiment according to FIGS. 7 to 9, connections 19 are located on the front sides. Housing connection 17 on the longitudinal sides encloses end folds 17' of the two filter elements 15,16 in a particle-tight manner thereby e.g. by means of clamping and/or ultrasound welding.

Filter element 16 consists here of upstream microporous membrane 8 and support fleece 9 according to FIG. 2, which are pleated in common to a fold packet. This results for upstream filter element 15 in a greater number of folds and adsorption surface in comparison to filter element 16.

All embodiments exhibit the common feature that large adsorption and filter areas are housed in a very close space with low dead volume. In contrast to round filter cartridges according to the state of the art with fold openings which widen out radially, the fold openings are located close to each other in this instance both on the retentate side, i.e., adsorption side and on the permeate side in order to reduce the dead volume and change into low-volume flow chambers.

We claim:

1. Multi-layer-filter composite (6) adaptable for enclosement in a housing (1, 2) comprising; means for separating precipitates containing cholesterol from blood plasma in one step prior to recirculation of said blood plasma, including, a hydrophobic pleated filter fleece medium (7) with precipitate absorbing properties and having narrow fold opening, a microporous hydrophilic membrane (8) downstream from (7) to control pressure conditions in the filter element and a draining hydrophilic support fleece layer (9), which is positively charged.

2. Filter according to claim 1, wherein said positively charged medium (9) is an adsorption medium on a side of the microporous membrane (8) facing away from the hydrophobic medium (7), which is an adsorption medium.

3. Filter element according to claim 2, wherein the positively charged adsorption medium (9) is formed by a membrane or fleece with anion-exchanger properties.

4. Filter according to claim 1 wherein the hydrophobic adsorption medium (7) is formed from a polyester continuous-filament fleece.

5. Filter element according to claim 1 wherein the hydrophilic, microporous membrane (8) is formed by a nylon membrane.

6. A filter housing unit wherein the filter of claim 1, is disposable and has a pleated membrane filter element (16) formed from a filter sheet having drainage layers that are closely folded.

7. Disposable filter unit according to claim 6, wherein an adsorbing filter element (15) and membrane filter element (16) immediately follow one another as a fold packet without a collecting line.

8. Disposable filter housing unit of claim 6 wherein a filter element (15') with adsorption properties is located after membrane filter element (16).

9. Disposable filter housing unit of claim 6 wherein the housing is constructed with at least two oblong housing shells (12, 12), fold edges of fold packets (15, 15', 16) run in a longitudinal direction of the housing, supply and removal connection (19, 19) change into distributors (19') running transversally over the fold edges, end folds of fold packets (15, 15', 16) sealingly contact longitudinal walls of housing shells (12, 12) and annular housing part (13) and front sides of the fold packets (15, 15', 16) are sealed on front sides (14) of the housing.

10. Disposable filter housing unit according to claim 6 wherein the housing consists of: a central housing, annular housing part (13) and two shell parts (12) which enclose filter elements (15, 15', 16) and are sealingly connected to each other.

11. Disposable filter housing unit according to claim 6 wherein housing parts (12, 13) are made of plastic and the latter and filter elements (15, 15', 16) are permanently connected.

12. Disposable unit according to claim 6 wherein housing parts (12, 13) are connected by welding.

13. Disposable unit according to claim 6 having end folds (17') of fold packets (15, 15', 16) sealed by pressure seals (7) of annular housing part (13).

14. Disposable unit according to claim 6 wherein front surfaces of fold packets (15, 15', 16) are sealed by a plastic mass (14) which is injected into the housing (12, 13).

15. Disposable unit according to claim 6 wherein end folds (17') of filter elements (15, 16) are enclosed particle-tight in housing connection (17) on longitudinal sides.

16. Disposable unit according to claim 15, wherein the end folds (17') are held in a sealing relationship between longitudinal flanges of housing parts (12, 12) by clamping, housing parts (12, 12) are connected by ultrasound welding.

* * * * *